(12) United States Patent
Ishikawa

(10) Patent No.: US 10,201,449 B2
(45) Date of Patent: Feb. 12, 2019

(54) SEX TOY HOLDER

(71) Applicant: Masakazu Ishikawa, Toyonaka (JP)

(72) Inventor: Masakazu Ishikawa, Toyonaka (JP)

( * ) Notice: Subject to any disclaimer, the term of this patent is extended or adjusted under 35 U.S.C. 154(b) by 0 days.

(21) Appl. No.: 15/782,166

(22) Filed: Oct. 12, 2017

(65) Prior Publication Data

US 2018/0104088 A1 Apr. 19, 2018

(30) Foreign Application Priority Data

Oct. 13, 2016 (JP) .................................. 2016-201861

(51) Int. Cl.
*A61F 5/41* (2006.01)
*A61H 19/00* (2006.01)
*A61H 21/00* (2006.01)

(52) U.S. Cl.
CPC ............... *A61F 5/41* (2013.01); *A61H 19/32* (2013.01); *A61H 21/00* (2013.01); *A61H 19/44* (2013.01); *A61H 2201/0119* (2013.01); *A61H 2201/1635* (2013.01)

(58) Field of Classification Search
CPC .................... A61H 19/44; A61H 19/50; A61H 2201/0153; A61H 2201/1253
See application file for complete search history.

(56) References Cited

U.S. PATENT DOCUMENTS

| | | | |
|---|---|---|---|
| 5,690,604 A * | 11/1997 | Barnett | A61H 19/44 248/229.15 |
| 6,203,491 B1 | 3/2001 | Uribe | |
| 7,056,281 B2 | 6/2006 | Bookwalter et al. | |
| 9,022,924 B1 * | 5/2015 | Thrasher | A61H 19/44 600/38 |
| 2005/0187431 A1 | 8/2005 | Hudson | |
| 2011/0190575 A1 | 8/2011 | McGough | |
| 2012/0323068 A1 | 12/2012 | Atchinson et al. | |
| 2013/0226045 A1 | 8/2013 | Li | |

FOREIGN PATENT DOCUMENTS

| | | |
|---|---|---|
| JP | 2007-296300 A | 11/2007 |
| JP | 3193973 U | 10/2014 |
| JP | 2015-139626 A | 8/2015 |

* cited by examiner

*Primary Examiner* — Christine H Matthews
(74) *Attorney, Agent, or Firm* — Rabin & Berdo, P.C.

(57) ABSTRACT

A sex toy holder is provided to be capable of holding a sex toy, and is used for action using the sex toy to obtain sexual pleasure, and includes a gripping portion that is gripped by a user during the action, and extends along a predetermined direction, two leg portions arranged side by side at a distance along the predetermined direction and provided so that a center of the gripping portion and a center between the two leg portions match each other in the predetermined direction, and a support portion that supports the two leg portions and the gripping portion.

7 Claims, 14 Drawing Sheets

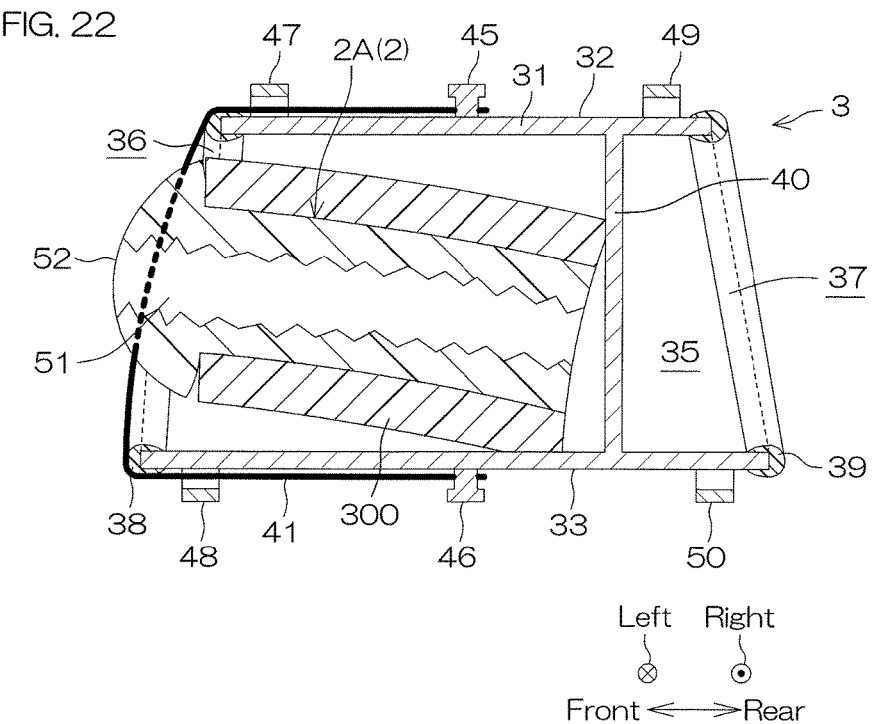

SEX TOY HOLDER

BACKGROUND OF THE INVENTION

1. Field of the Invention

The present invention relates to a sex toy holder capable of holding a sex toy.

2. Description of Related Art

Conventionally, sex toys to be used for obtaining sexual pleasure by stimulating a genitalia or a body have been known. Sex toys are used for, for example, masturbation. Japanese Patent Application Publication No. 2015-139626 and Japanese Registered Utility Model Publication No. 3193973 disclose male genitalia massage apparatuses for massage of a male genitalia. In the male genitalia massage apparatus, when a male genitalia is inserted into a receptacle, and a user moves the receptacle back and forth, ejaculation is promoted. Also, Japanese Patent Application Publication No. 2007-296300 discloses a female genitalia massage apparatus. When a user inserts the female genitalia massage apparatus into the vagina and moves the female genitalia massage apparatus in this state, the inside of the vagina is stimulated. It is recognized that use of these sex toys is useful for improvement in sexual dysfunction and frigidity as well as for obtaining sexual pleasure.

SUMMARY OF THE INVENTION

In the male genitalia massage apparatuses described in Japanese Patent Application Publication No. 2015-139626 and Japanese Registered Utility Model Publication No. 3193973 and the female genitalia massage apparatus described in Japanese Patent Application Publication No. 2007-296300, at the time of use, a user directly grips a sex toy by hand (for example, one hand), and in this state, makes it move in a reciprocating motion in the back and forth direction. There is a problem in which this reciprocating motion increases the burden on the arm of the user, and easily fatigues the user.

Therefore, an object of the present invention is to provide a sex toy holder that enables action using a sex toy to obtain sexual pleasure while reducing the feeling of fatigue.

The present invention provides a sex toy holder that is provided to be capable of holding a sex toy and is used for action using the sex toy to obtain sexual pleasure, including a gripping portion that is gripped by a user during the action, and extends along a predetermined direction, two leg portions arranged side by side at a distance along the predetermined direction and provided so that a center of the gripping portion and a center between the two leg portions match each other in the predetermined direction, and a support portion that supports the two leg portions and the gripping portion.

With this arrangement, According to the reciprocating rocking of the sex toy holder, the sex toy held by the sex toy holding device reciprocates with respect to the user. At this time, the weight of the sex toy is borne by the two leg portions and that function as fulcrums. Therefore, the burden on the arm of the user can be reduced. Accordingly, action using a sex toy to obtain sexual pleasure can be performed while reducing the feeling of fatigue.

Also, the sex toy holder is reciprocated with two leg portions as fulcrums. Since the two legs are the fulcrum, the wobble of the sex toy holder is suppressed. Therefore, the reciprocating movement of the sexual instrument draws a stable trajectory. Further, in an extending direction of the gripping portion, the center of the gripping portion and the center between the two leg portions match each other, the load on the sex toy holder can be dividedly borne by the two leg portions. With these, it is possible to cause the sexual instrument to reciprocate in a stable state on action using the sex toy to obtain sexual pleasure.

Thus, as a result of reciprocating motion of the sex toy while reducing the feeling of fatigue and in a stable state, the user can concentrate on action using the sex toy to obtain sexual pleasure, and the user obtain greater sexual pleasure.

Also, the support portion may include a pair of columns which have the leg portions on one side end portions, and one end sides of which are joined turnably to each other, and the gripping portion may include a fastening portion that fastens the other sides of the pair of columns to each other.

Also, the fastening portion may include a ring member that encloses the pair of columns, and the columns may be provided with tapers so that a distance between side edges of the pair of columns on the sides not facing each other changes along extending directions of the columns.

Also, the sex toy holder may further include a sex toy holding device to hold the sex toy, and the support portion may support the sex toy holding device.

The support portion may support the sex toy holding device so that the sex toy holding device is movable up and down and/or changeable in posture.

The support portion may include a pair of columns respectively having the leg portions on one side end portions, and the sex toy holding device may be supported by the columns by fastening the other sides of the pair of columns to each other in a state where the sex toy holding device is sandwiched between the pair of columns.

The above-described or other objects, features, and effects of the present invention will be clarified by the description of the preferred embodiments given below with reference to the accompanying drawings.

BRIEF DESCRIPTION OF THE DRAWINGS

FIG. 22 is a sectional view for describing a modification of the present invention.

DETAILED DESCRIPTION OF PREFERRED EMBODIMENTS

Figure 1:
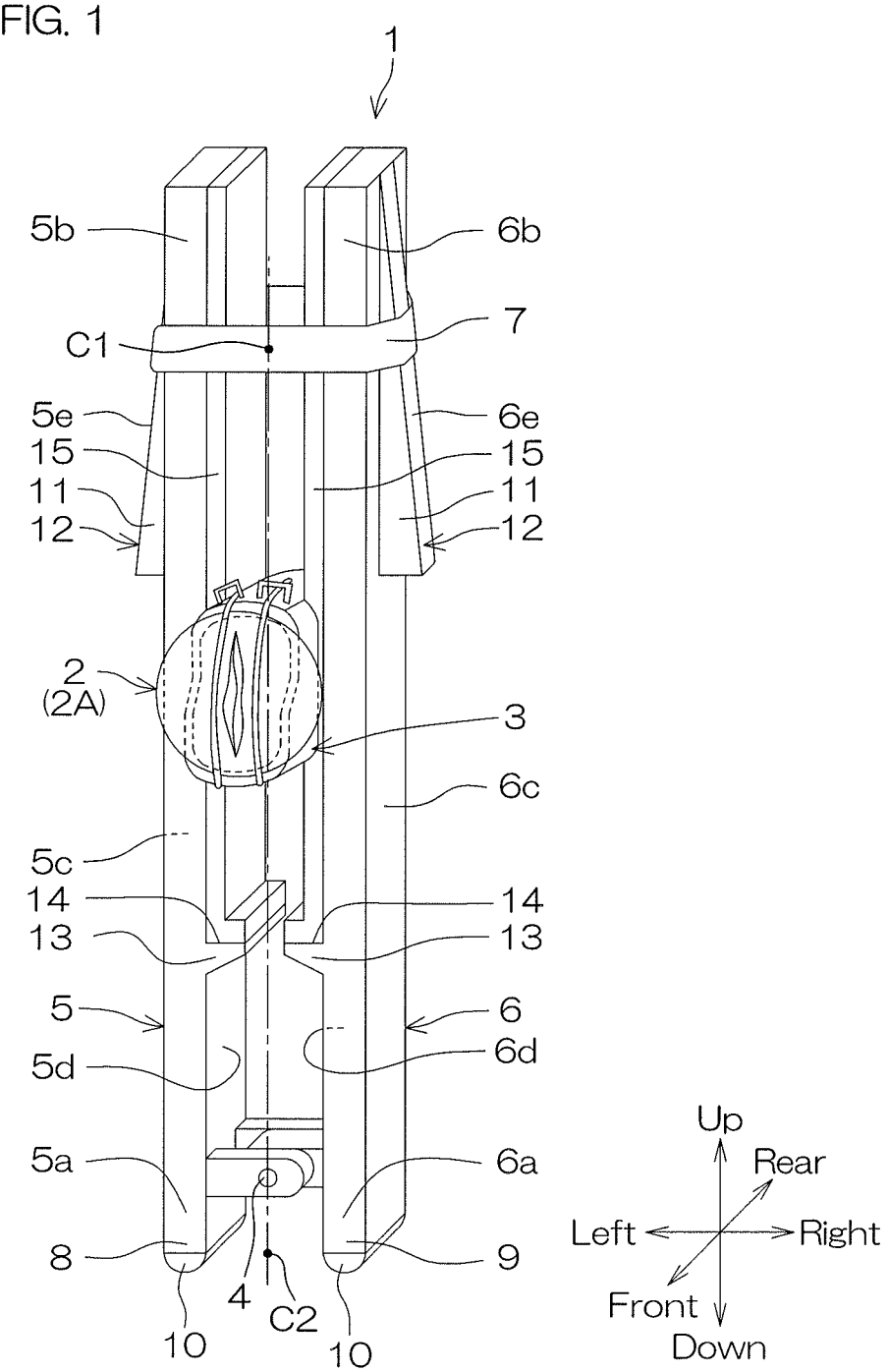
FIG. 1 is a perspective view of a sex toy holder according to a first preferred embodiment of the present invention.

FIG. 1 is a perspective view of a sex toy holder 1 according to a first preferred embodiment of the present invention.

The sex toy holder 1 is a holder to be used by a user for action using a sex toy 2 (the sex toy 2 is a general term including the sex toy 2A for a male (refer to FIG. 1 and FIG. 8) and the sex toy 2B for a female (refer to FIG. 12.)) to obtain sexual pleasure (for example, masturbation). Hereinafter, description will be given by defining a user side during masturbation using the sex toy holder 1 as the "front side," and the side opposite to the user side as the "rear side." Also, the description will be given by defining a left side as viewed from the user as the "left side," and a right side as viewed from the user as the "right side" (the same applies to the second and third preferred embodiments).

The sex toy holder 1 includes two leg portions 8 and 9, a gripping portion to be gripped by a user, and a support portion (joining portion) that supports (joins) the leg portions 8 and 9 and the gripping portion.

More specifically, the sex toy holder 1 includes a sex toy holding device 3 to hold a sex toy 2, a pair of columns (a first column 5 and a second column 6) whose end portions on one end sides (upper end portions in FIG. 1) are joined turnably around a turning shaft 4, and a fastening member 7 that fastens end portions on the other sides (lower end portions in FIG. 1) of the pair of columns 5 and 6 to each other. At one side end portion 5a of the first column 5, a first leg portion 8 to stand the sex toy holder 1 is provided. At one side end portion 6a of the second column 6, a second leg portion 9 to stand the sex toy holder 1 is provided. In the right-left direction (predetermined direction), a center C1 of the fastening member 7 (gripping portion) and a center C2 between the first and second leg portions 8 and 9 match each other. To a lower end of each of the leg portions 8 and 9, a half-column-shaped pad 10 is attached.

By fastening the other side end portions 5b and 6b of the pair of columns 5 and 6 to each other by the fastening member 7 in a state where the sex toy holding device 3 is sandwiched between the pair of columns 5 and 6, the sex toy holding device 3 is supported by the pair of columns 5 and 6. In this preferred embodiment, the pair of columns 5 and 6 function as support portions (joining portions).

The fastening member 7 includes a ring member that encloses and tightens the other side end portions 5b and 6b of the pair of columns 5 and 6 together. The fastening member formed of the ring member is a longitudinal member longitudinal along the right-left direction (predetermined direction) in a state where it is fitted to the pair of columns 5 and 6. The fastening member 7 functions as the gripping portion to be gripped by a user during masturbation using the sex toy 2.

Figure 2:
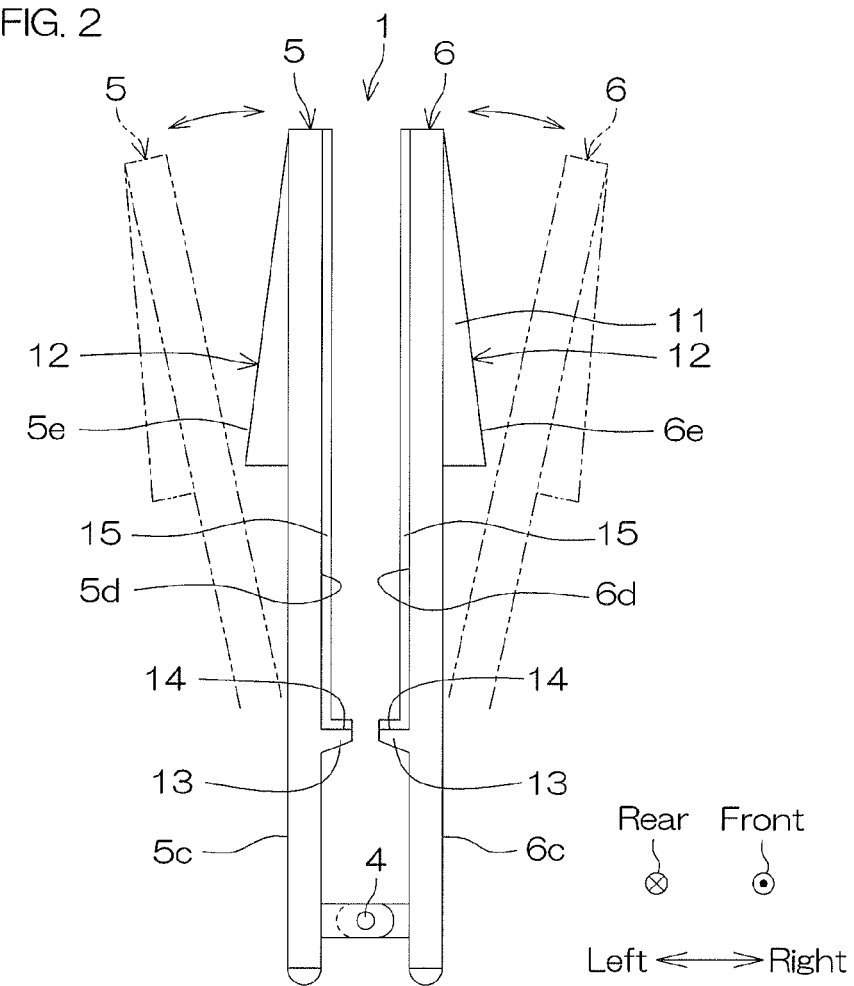
FIG. 2 is a front view of a pair of columns included in the sex toy holder.

FIG. 2 is a front view of the pair of columns 5 and 6 included in the sex toy holder 1. With reference to FIG. 1 and FIG. 2, the pair of columns 5 and 6 will be described. Each of the columns 5 and 6 is made of wood, a synthetic resin, or metal. A sectional shape of each of the columns 5 and 6 orthogonal to the longitudinal direction is rectangular. One side end portions 5a and 6a of the pair of columns 5 and 6 are joined to each other turnably around the turning shaft 4. Therefore, as shown in FIG. 2, in a free state of the columns 5 and 6, the other side end portions 5b and 6b can be separated from each other.

In the respective columns 5 and 6, on opposite side surfaces 5c and 6c on the sides opposite to the sides facing each other, tapered projections 11 projecting toward the sides opposite to the sides facing each other are provided. The tapered projections 11 are formed across the regions from the other ends of the columns 5 and 6 (lower ends in FIG. 1 and FIG. 2) to approximately ⅔ of the entire lengths (these regions are referred to as the other side end portion 5b and the other side end portion 6b), and project from portions except for the front and rear ends in the thickness direction (front-rear direction) in the opposite side surfaces 5c and 6c. That is, the sectional shapes of the columns 5 and 6 in the other side end portions 5b and 6b are T shapes directed to project in directions separating from each other. The tapered projections 11 are provided so that their projecting amounts increase downward, and assume right triangles in a front view. That is, at side edges 5e and 6e on the sides not facing each other in the pair of columns 5 and 6, tapers 12 that narrow the side edges 5e and 6e on the sides not facing each other toward the other side end edges (upper sides in FIG. 1 and FIG. 2) in the other side end portions 5b and 6b are provided.

In the respective columns 5 and 6, on facing side surfaces 5d and 6d on the sides facing each other, coming-off preventive projections 13 projecting toward the facing sides from the entire regions in the front-rear direction are provided. The pair of coming-off preventive projections 13 are provided at positions close to one ends from the central portions in the longitudinal directions of the respective columns 5 and 6 (for example, regions from one ends to ⅓ of the entire lengths). Tip end portions of the pair of coming-off preventive projections 13 are disposed so as to face each other across a predetermined gap. On the respective coming-off preventive projections 13, catching surfaces 14 orthogonal to the facing side surfaces 5d and 6d are formed.

In a state where the columns 5 and 6 sandwich the sex toy holding device 3, if the distance between the other side end portions 5b and 6b of the pair of columns 5 and 6 becomes excessively large, the support of the sex toy holding device 3 by the columns 5 and 6 is released, and the sex toy holding device 3 may drop. Even if the sex toy holding device 3 drops, the sex toy holding device 3 can be caught by the catching surfaces 14.

On the facing side surfaces 5d and 6d on the sides facing each other, cushioning sheets 15 are disposed in entire regions close to the other end sides relative to the coming-off preventive projections 13. The cushioning sheets 15 are formed by using, for example, foamed rubber (NBR foamed rubber, acrylic foam rubber, silicone foam rubber, fluorine foam rubber, etc.). Therefore, damage to the sex toy holding device 3 sandwiched by the facing side surfaces 5d and 6d can be suppressed or prevented. The cushioning sheets 15 are disposed not only on the facing side surfaces 5d and 6d but also on the front surfaces of the catching surfaces 14. Therefore, damage to the sex toy holding device 3 caught by the catching surfaces 14 can be suppressed or prevented.

On one side end portion 5a of the first column 5, a pair of outer projections 16 projecting rightward from the respective front and rear ends, are provided. On one side end portion 6a of the second column 6, one inner projection 17 projecting leftward from the central portion except for the front and rear ends, is provided.

Figure 3:
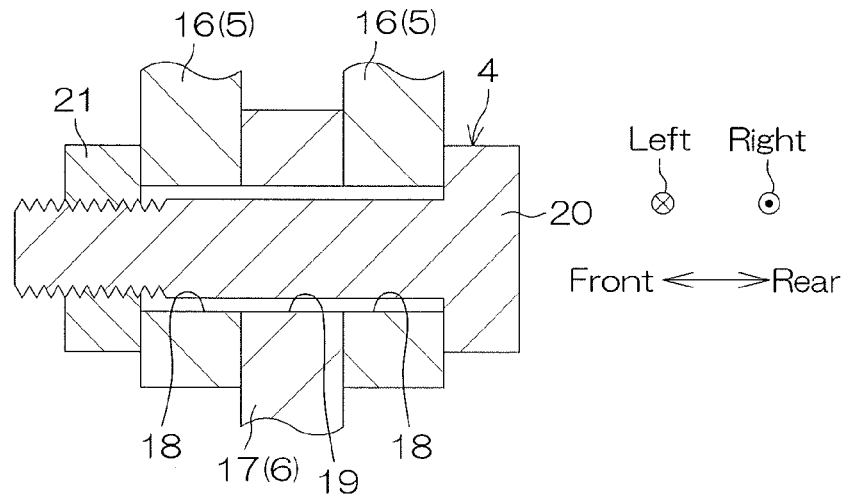
FIG. 3 is a sectional view showing an arrangement of a turning shaft included in the sex toy holder.

FIG. 3 is a sectional view showing an arrangement of the turning shaft 4. The turning shaft 4 includes a bolt 20 attached to penetrate through screw insertion holes 18 and a screw insertion hole 19 in the right-left direction, and a nut 21 that is fastened to the tip end of the bolt 20 and prevents the bolt 20 from coming off from the screw insertion holes 18 and 19. The insertion holes 18 are provided in the respective outer projections 16. The screw insertion hole 19 is provided in the inner projection 17. As the turning shaft 4, another arrangement (for example, a hinge mechanism) may be adopted.

Figure 4:
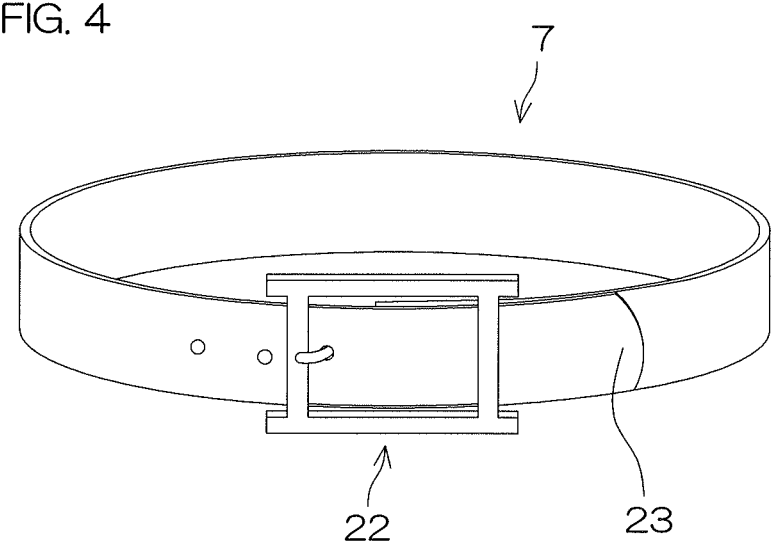
FIG. 4 is a view showing an arrangement of a fastening member included in the sex toy holder.

FIG. 4 is a view showing an arrangement of the fastening member 7.

The fastening member 7 includes a belt 23 and a buckle 22 provided on one end portion of the belt 23. A material of the belt 23 is a material that hardly stretches (leather, fiber, etc.). As the buckle 22, the pin buckle shown in FIG. 4 may be adopted. At least one pin engagement hole is sufficient to be provided in the belt 23, however, to enable sex toy holding devices 3 with different sizes to be supported by the columns 5 and 6, a plurality of pin engagement holes may be formed so that the length of the belt 23 is adjustable. The belt 23 may be endless, and in this case, the buckle 22 is not used.

As shown in FIG. 1, the perimeter of the fastening member 7 is set to a length that can enclose the entire circumference of the first and second columns 5 and 6 in a region in which the tapered projections 11 are not provided, but cannot enclose the entire circumference of the first and second columns 5 and 6 at the highest positions of the tapered projections 11. Therefore, by moving the fastening member 7 enclosing the tapered projections 11 toward one side end portions 5a and 6a of the columns 5 and 6, the fastening member 7 tightens the other side end portions 5b and 6b of the columns 5 and 6 and can fasten (that is, close) the other side end portions 5b and 6b of the columns 5 and 6. On the contrary, by moving the fastening member 7 enclosing the tapered projections 11 toward the other side end edges (upper sides in FIG. 1 and FIG. 2) of the columns 5 and 6, tightening of the other side end portions 5b and 6b of the columns 5 and 6 by the fastening member 7 loosens and fastening of the other side end portions 5b and 6b of the columns 5 and 6 can be released (that is, opened).

Figure 5:
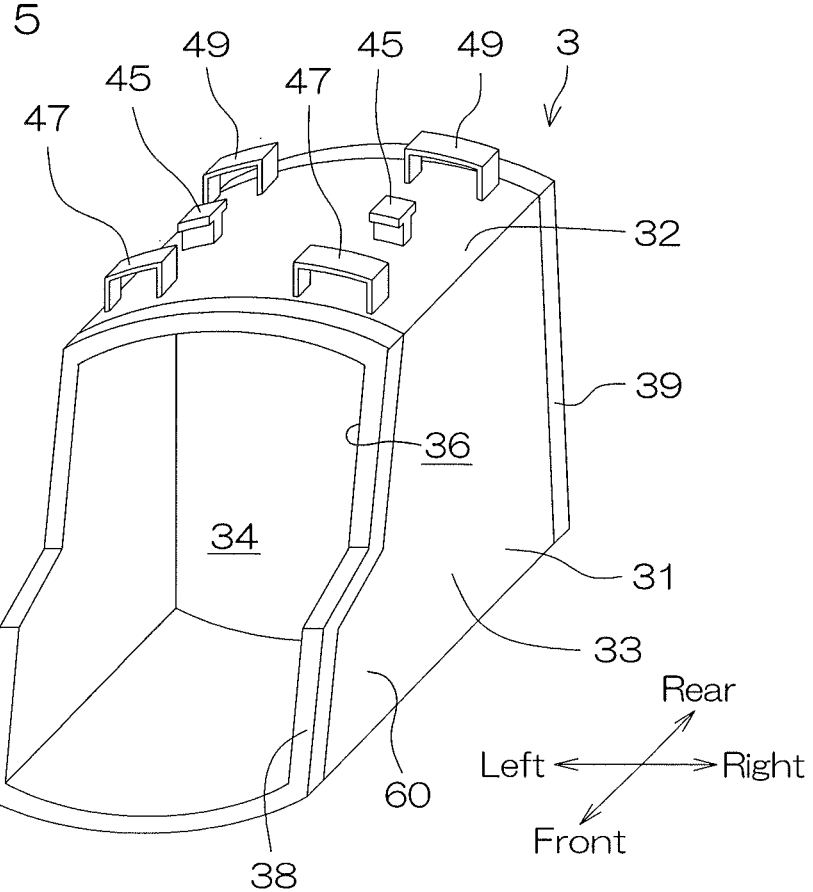
FIG. 5 is a perspective view showing an arrangement of a sex toy holding device included in the sex toy holder.
Figure 6:
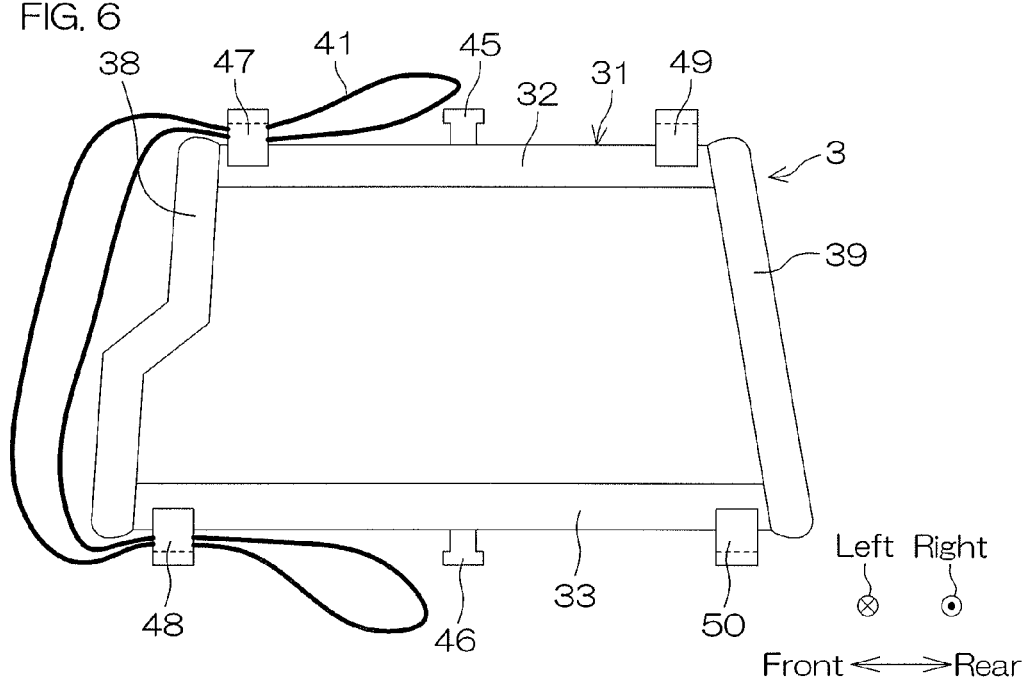
FIG. 6 is a side view for describing attachment of a coming-off preventive member to the sex toy holding device in a first usage pattern of the sex toy holder.
Figure 7:
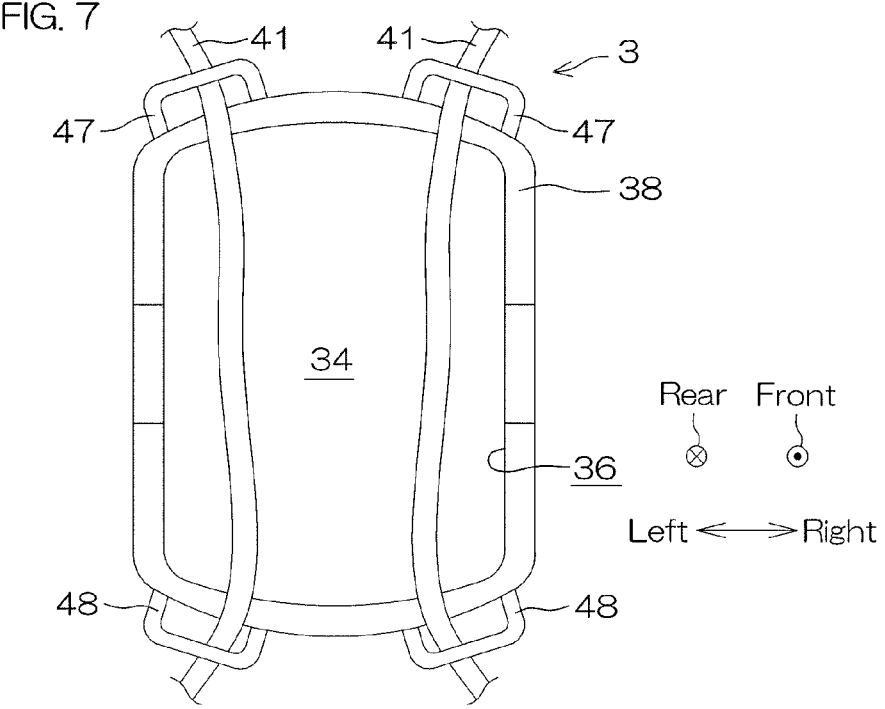
FIG. 7 is a front view of the sex toy holding device in an attached state of the coming-off preventive members.
Figure 8:
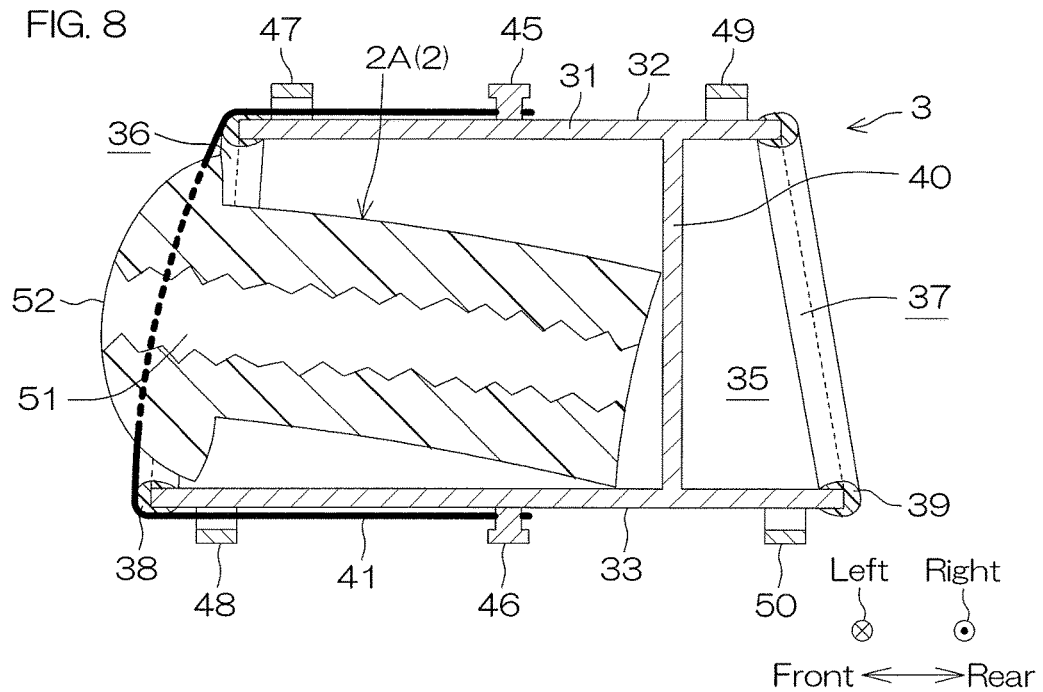
FIG. 8 is a sectional view showing a fitting state of a first sex toy to the sex toy holding device in the first usage pattern of the sex toy holder.
Figure 9:
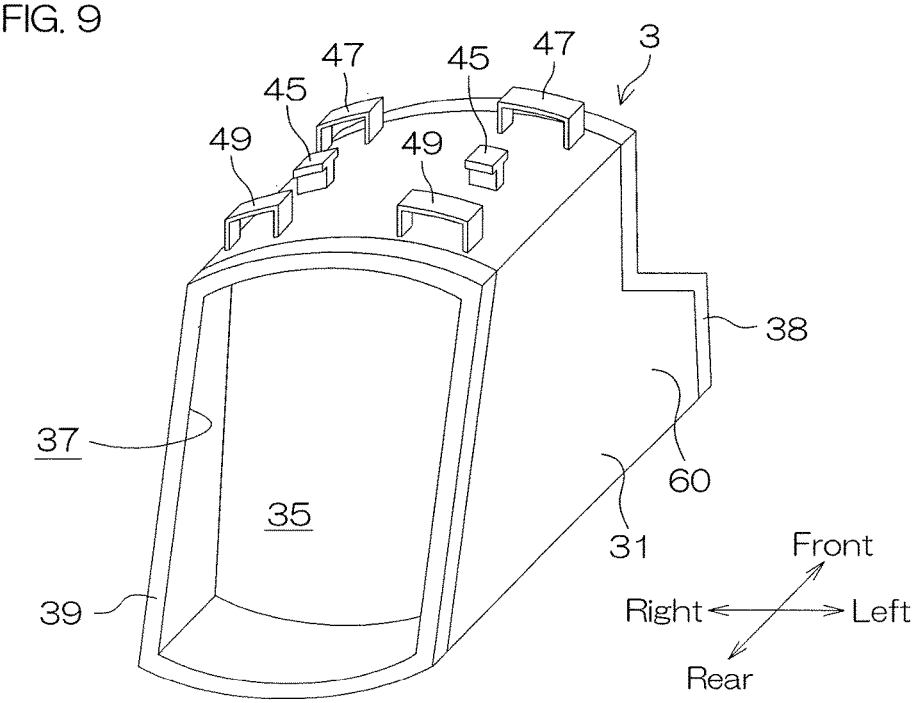
FIG. 9 is a perspective view of an arrangement of the sex toy holding device, viewed from a direction different from that in FIG. 5.
Figure 10:
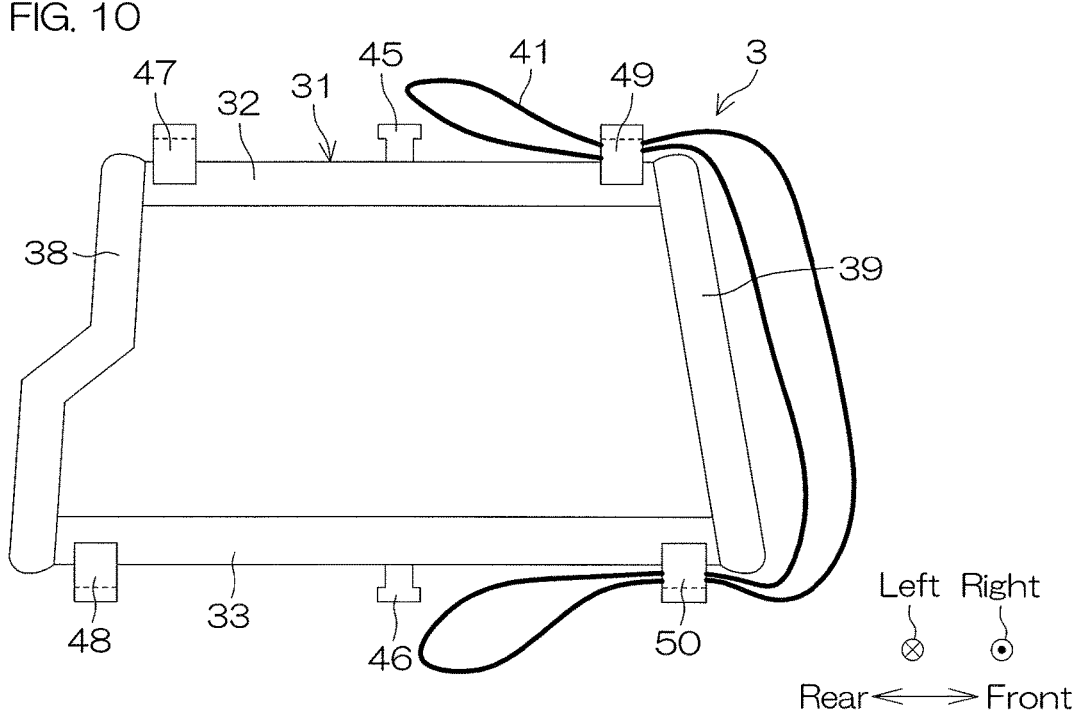
FIG. 10 is a side view for describing attachment of the coming-off preventive member to the sex toy holding device in a second usage pattern of the sex toy holder.
Figure 11:
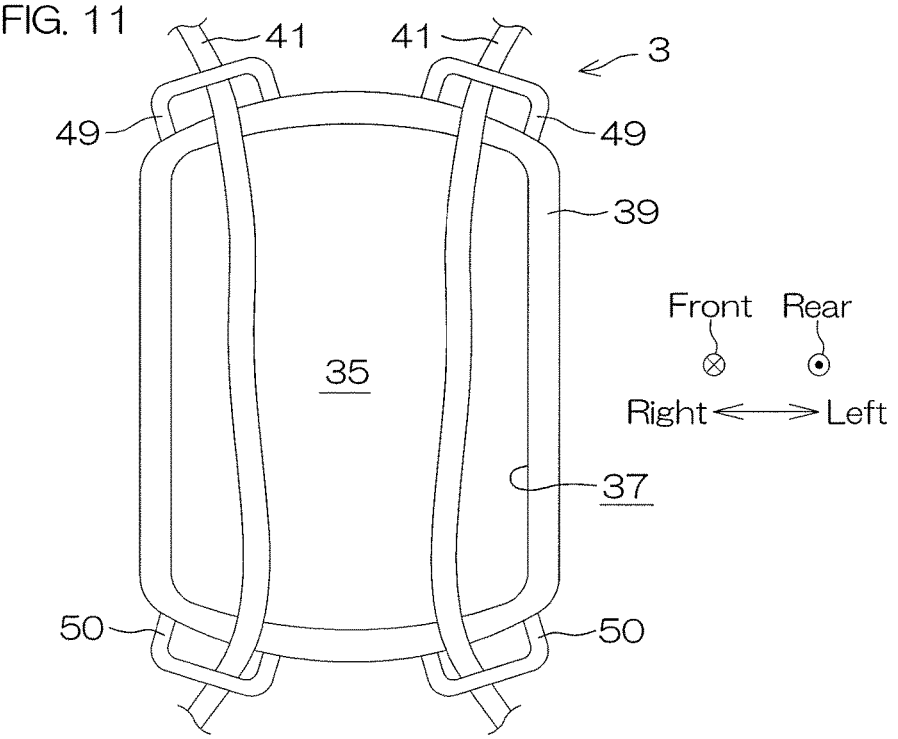
FIG. 11 is a back view of the sex toy holding device in an attached state of the coming-off preventive members.
Figure 12:
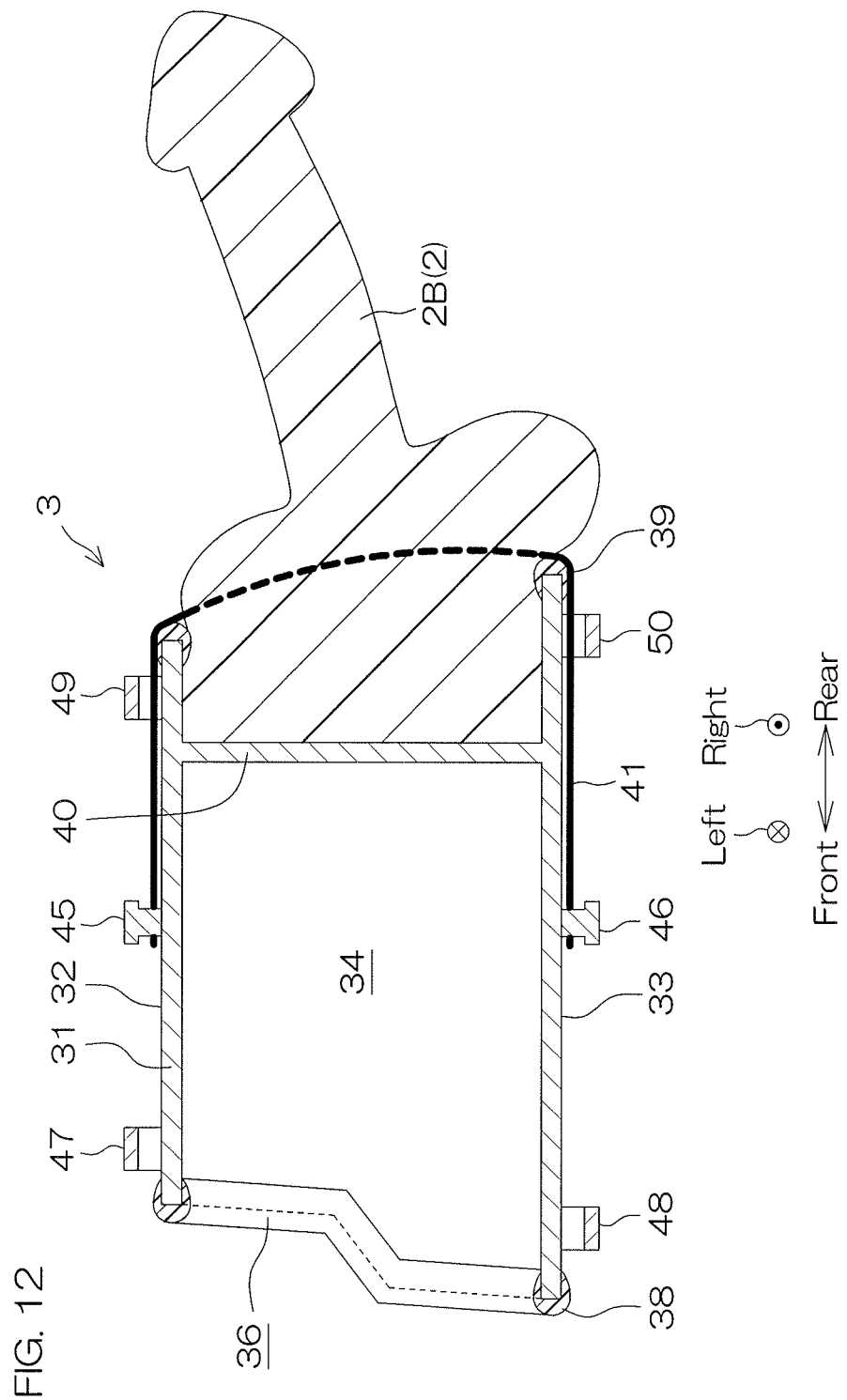
FIG. 12 is a sectional view showing a fitting state of a second sex toy to the sex toy holding device in the second usage pattern of the sex toy holder.

FIG. 5 is a perspective view showing an arrangement of the sex toy holding device 3. FIG. 6 is a side view for describing attachment of the coming-off preventive member 41 to the sex toy holding device 3 in a first usage pattern of the sex toy holder 1. FIG. 7 is a front view of the sex toy holding device 3 in an attached state of the coming-off preventive members 41. FIG. 8 is a sectional view showing a fitting state of a sex toy 2A for a male to the sex toy holding device 3 in the first usage pattern of the sex toy holder 1. FIG. 9 is a perspective view of the arrangement of the sex toy holding device 3, viewed from a direction different from that in FIG. 5. FIG. 10 is a side view for describing attachment of the coming-off preventive members 41 to the sex toy holding device 3 in a second usage pattern of the sex toy holder 1. FIG. 11 is a back view of the sex toy holding device 3 in an attached state of the coming-off preventive members 41. FIG. 12 is a sectional view showing a fitting state of a sex toy 2B for a female to the sex toy holding device 3 in the second usage pattern of the sex toy holder 1. The sex toy holding device 3 will be described with reference to FIG. 5 to FIG. 12. The sex toy 2A for a male and the sex toy 2B for a female are distribution items that are distributed as products in a market. In this case, the user retrofits the sex toy 2A for a male and the sex toy 2B for a female to the sex toy holding device 3. The sex toy 2A for a male and/or the sex toy 2B for a female may be dedicated exclusive items used for the sex toy holder 1.

The sex toy holding device 3 includes a main body portion 31 formed of a substantially quadrangular cylindrical body having open front and rear ends. The main body portion 31 has, on outer surfaces, an upper surface 32 and a lower surface 33 each having an arc-shaped section projecting outward. The main body portion 31 is formed by using a hard resin (PVC, polypropylene, polyethylene, polystyrene, etc.) or a metal (stainless steel, sheet metal, etc.). The main body portion 31 is provided to be capable of accommodating and holding both of the sex toy 2A for a male (refer to FIG. 1 and FIG. 8) and the sex toy 2B for a female (refer to FIG. 12). The inside of the main body portion 31 includes a first accommodation chamber 34 to accommodate the sex toy 2A for a male and a second accommodation chamber 35 to accommodate the sex toy 2B for a female. An opening on the front side of the main body portion 31 is a first accommodation opening 36 to make the sex toy 2A for a male be accommodated in the first accommodation chamber 34, and an opening on the rear side of the main body portion 31 is a second accommodation opening 37 to make the sex toy 2B for a female be accommodated in the second accommodation chamber 35. In a front view, the centers of the openings of the main body portion 31 (the opening on the front side and the opening on the rear side) are included in a line segment connecting the center C1 and the center C2.

On a front end portion of the main body portion 31, a receiving portion 60 to receive a front end portion of the sex toy 2A for a male from below is provided to project forward. The receiving portion 60 is provided integrally with the main body portion 31. The front end portion of the sex toy 2A for a male swells as compared with other portions. Therefore, in an accommodated state of the sex toy 2A for a male in the first accommodation chamber 34, the front end portion of the sex toy 2A for a male protrudes from the first accommodation opening 36. By receiving the front end portion of the sex toy 2A for a male by the receiving portion 60, the front end portion of the sex toy 2A for a male can be prevented from drooping, so that the sex toy 2A for a male can be excellently held by the sex toy holding device 3.

At a front end edge of the main body portion 31, that is, at an outer rim of the first accommodation opening 36, in the entire region thereof, a first protection material 38 is disposed across the outer rim of the first accommodation opening 36. At a rear end edge of the main body portion 31, that is, at an outer rim of the second accommodation opening 37, in the entire region thereof, a second protection material 39 is disposed across the outer rim of the second accommodation opening 37. The first and second protection materials 38 and 39 are formed by using, for example, foamed rubber (for example, NBR foamed rubber, acrylic foam rubber, silicone foam rubber, fluorine foam rubber, etc.). When using the sex toy holder 1, the outer rim of the first accommodation opening 36 or the outer rim of the second accommodation opening 37 may come into contact with the male genitalia or the lower abdomen of a user, and to prevent the user from being injured, the first and second protection materials 38 and 39 are disposed.

The first and second accommodation chambers 34 and 35 are partitioned by a tabular partition 40 (refer to FIG. 8) that comparts the inside of the sex toy holding device 3 into front and rear portions. The first accommodation chamber 34 is set to such a size that can accommodate the sex toy 2A for a male (refer to FIG. 1 and FIG. 8), and the second accommodation chamber 35 is set to such a size that can accommodate a base portion of the sex toy 2B for a female (refer to FIG. 12). The first accommodation chamber 34 is provided to be larger than the second accommodation chamber 35.

In order to prevent the sex toy 2 from coming off from the inside of the main body portion 31, the sex toy holding device 3 further includes coming-off preventive members 41 that close portions of the accommodation openings 36 and 37, and coming-off preventive member support portions that make the coming-off preventive members 41 be supported by the main body portion 31.

In this preferred embodiment, a pair of coming-off preventive members 41 are provided. The pair of coming-off preventive members 41 may be arranged side by side in the right-left direction as shown in FIG. 7 and FIG. 11, or may be arranged one above the other. The coming-off preventive members 41 are long bodies with elasticity. As long bodies, for example, long bodies made of rubber are adopted, and in the present preferred embodiment, rubber bands are adopted as long bodies. However, long bodies made of a material other than rubber may be adopted.

The coming-off preventive member support portions include first coming-off preventive member support portions to support the coming-off preventive members 41 across the first accommodation opening 36, and second coming-off preventive member support portions to support the coming-off preventive members 41 across the second accommodation opening 37.

The first coming-off preventive member support portions that are provided one to one corresponding to the coming-off preventive members 41 are provided as a pair of right and left first coming-off preventive member support portions. The first coming-off preventive member support portion includes an upper end latch portion 45 on which an upper end of the coming-off preventive member 41 is latched, a lower end latch portion 46 on which a lower end of the coming-off preventive member 41 is latched, a first upper insertion portion 47 through which the coming-off preventive member 41 is inserted, and a first lower insertion portion 48 through which the coming-off preventive member 41 is inserted. The upper end latch portion 45 is fixed to a middle portion of the upper surface 32 in the front-rear direction, and the lower end latch portion 46 is fixed to a middle portion of the lower surface 33 in the front-rear direction. The first upper insertion portion 47 and the first lower insertion portion 48 are formed of frame bodies. The first upper insertion portion 47 is fixed to a front end portion of the upper surface 32, and the first lower insertion portion 48 is fixed to a front end portion of the lower surface 33.

The second coming-off preventive member support portions that are provided one to one corresponding to the coming-off preventive members 41 are provided as a pair of right and left second coming-off preventive member support portions. The second coming-off preventive member support portion includes an upper end latch portion 45, a lower end latch portion 46, a second upper insertion portion 49 through which the coming-off preventive member 41 is inserted, and a second lower insertion portion 50 through which the coming-off preventive member 41 is inserted. The second upper insertion portion 49 and the second lower insertion portion 50 are formed of frame bodies. The second upper insertion portion 49 is fixed to a rear end portion of the upper surface 32, and the second lower insertion portion 50 is fixed to a front end portion of the lower surface 33.

In the present preferred embodiment, the upper end latch portions 45 and the lower end latch portions 46 assume T shapes projecting forward and rearward in a side view, and the coming-off preventive members 41 can be latched thereon from any of the first accommodation opening 36 side and the second accommodation opening 37 side. That is, in the present preferred embodiment, the upper end latch portions 45 and the lower end latch portions 46 are used in common when attaching the coming-off preventive members 41 to the first accommodation opening 36 and when attaching the coming-off preventive members 41 to the second accommodation opening 37 side. However, the upper end latch portions and the lower end latch portions to be used may differ between when the coming-off preventive members 41 are attached to the first accommodation opening 36 side and when the coming-off preventive members 41 are attached to the second accommodation opening 37 side.

When the sex toy holding device 3 is used by accommodating the sex toy 2A for a male in the sex toy holding device 3 (hereinafter, the usage state at this time is referred to as a first usage state), as shown in FIG. 7, the pair of coming-off preventive members 41 are attached to the first accommodation opening 36 side. In detail, as shown in FIG. 6, an upper end of each coming-off preventive member 41 is latched on the upper end latch portion 45 via the first upper insertion portion 47, and a lower end of each coming-off preventive member 41 is latched on the lower end latch portion 46 via the first lower insertion portion 48. Accordingly, the pair of coming-off preventive members 41 are attached to the main body portion 31 so as to get across the first accommodation opening 36 vertically.

Then, a user makes the sex toy 2A for a male (refer to FIG. 8) be accommodated in the first accommodation chamber 34 via the first accommodation opening 36. Then, the user fits the pair of coming-off preventive members 41 to the sex toy 2A for a male from the front side. Accordingly, the sex toy 2A for a male can be prevented from coming off from the first accommodation chamber 34.

As shown in FIG. 8, the sex toy 2A for a male is in the shape of a female genitalia (vaginal orifice and vagina) to reproduce the feeling of insertion of a male genitalia into a female genitalia. The sex toy 2A for a male is formed by using, for example, a soft resin (for example, rubber, silicone, vinyl chloride, and thermoplastic elastomer, etc.). The sex toy 2A for a male is formed to have a tubular external shape with a predetermined length, and have a cylindrical hollow portion 51 formed inside. The hollow portion 51 opens at the front side, and has an insertion opening 52 corresponding to the vaginal orifice. A rear end of the hollow portion 51 is closed or opened. As the sex toy 2A for a male, a commercialized product is adopted, and various kinds may be adopted. At the time of masturbation, a user (male) inserts his male genitalia into the hollow portion 51 via the insertion opening 52.

When the sex toy holding device 3 is used by accommodating the sex toy 2B for a female (refer to FIG. 12) in the sex toy holding device 3 (hereinafter, the usage state at this time is referred to as a second usage state), as shown in FIG. 11, the coming-off preventive members 41 are attached so as to get across the second accommodation opening 37. Specifically, as shown in FIG. 10, an upper end of each coming-off preventive member 41 is latched on the upper end latch portion 45 via the second upper insertion portion 49, and a lower end of each coming-off preventive member 41 is latched on the lower end latch portion 46 via the second lower insertion portion 50. Accordingly, as shown in FIG. 11, the pair of coming-off preventive members 41 are attached to the main body portion 31 so as to get across the second accommodation opening 37.

Then, a user makes the sex toy 2B for a female (refer to FIG. 12) be accommodated in the second accommodation chamber 35 via the first accommodation opening 36. Then, the user fits the pair of coming-off preventive members 41 to the sex toy 2B for a female from the rear side, and accordingly, the sex toy 2B for a female can be prevented from coming off from the second accommodation chamber 35.

As shown in FIG. 12, the sex toy 2B for a female is in the shape of a male genitalia to reproduce the feeling of insertion of a male genitalia into a female genitalia. The sex toy 2B for a female may be made of a soft resin (for example, rubber, silicone, etc.). The sex toy 2B for a female includes a base portion and a projecting portion that projects from the base portion and is in the shape of a male genitalia.

Figure 13:
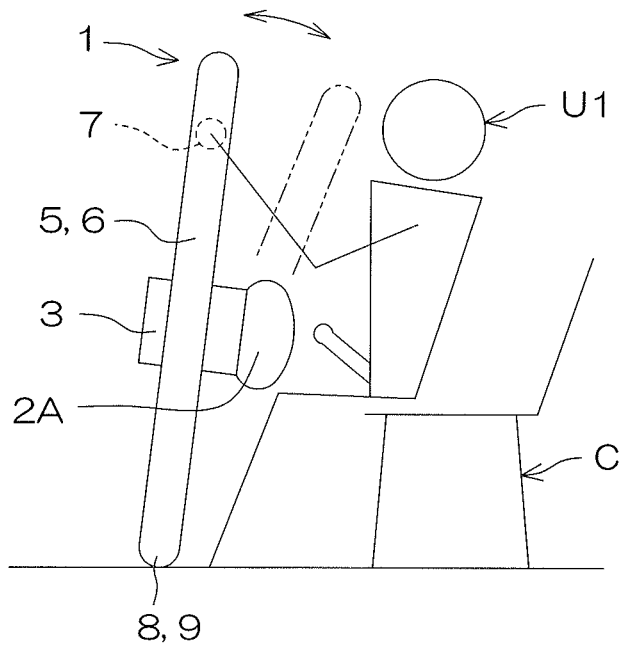
FIG. 13 is a schematic view showing a method for using the sex toy holder in the first usage pattern of this sex toy holder.

Next, a method for using the sex toy holder 1 will be described. FIG. 13 is a schematic view showing a method for using the sex toy holder 1 in the first usage pattern of the sex toy holder 1. In the first usage pattern of the sex toy holder 1, when a user (male user) U1 masturbates, for example, the user sits on the edge of a chair C and protrudes his pelvis forward, and in this state, the user stands, between his thighs, the sex toy holder 1 on the floor so that the two leg portions 8 and 9 are arranged side by side in the right-left direction (predetermined direction). The user U1 inserts his male genitalia into the inside of the sex toy 2A for a male. Then, the user U1 grips the fastening member 7 with one hand, and manually rocks the sex toy holder 1 in a reciprocating manner by using both of the two leg portions 8 and 9 as fulcrums. According to the reciprocating rocking of the sex toy holder 1, the sex toy 2A for a male reciprocates in the back and forth direction with respect to the male genitalia of the user U1. Accordingly, the user U1 can obtain pleasure. Since the user U1 sits on the edge of the chair C, the sex toy holder 1 can be prevented from coming into contact with the chair C during masturbation.

Figure 14:
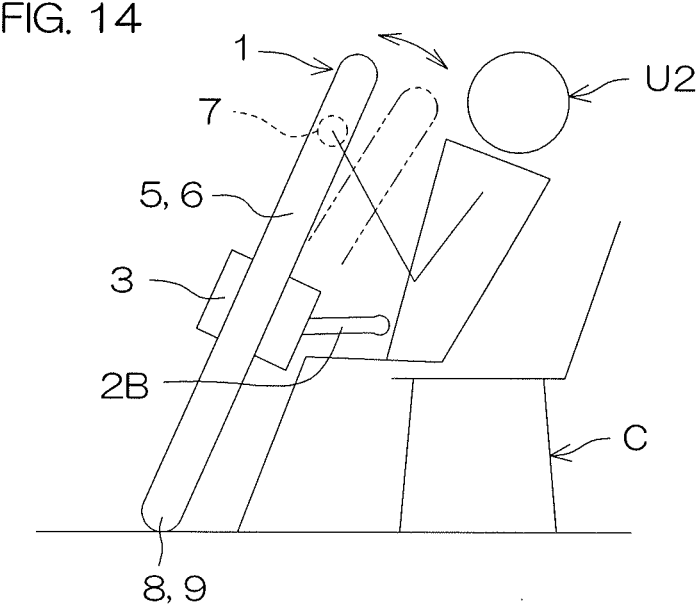
FIG. 14 is a schematic view showing another method for using the sex toy holder in the second usage pattern of this sex toy holder.

FIG. 14 is a schematic view showing a method for using the sex toy holder 1 in the second usage pattern of the sex toy holder 1. In the second usage pattern of the sex toy holder 1, the sex toy holder 1 is inverted in the front-rear direction from the first usage pattern. In the second usage pattern of the sex toy holder 1, when a user (female user) U2 masturbates (uses the sex toy holding device 3 in a state where the sex toy 2B for a female is accommodated in the sex toy holding device 3), for example, the user stands, between her thighs, the sex toy holder 1 on the floor so that the two leg portions 8 and 9 are arranged side by side in the right-left direction (predetermined direction) while sitting on a chair C. The user U2 inserts the sex toy 2B for a female into her female genitalia. Then, the user U2 grips the fastening member with one hand, and rocks the sex toy holder 1 in a reciprocating manner by using both of the two leg portions 8 and 9 as fulcrums. According to the reciprocating rocking of the sex toy holder 1, the sex toy 2B for a female reciprocates in the back and forth direction with respect to the female genitalia of the user U2. Accordingly, the user U2 can obtain pleasure. Since the user U2 sits on the edge of the chair C, the sex toy holder 1 can be prevented from coming into contact with the chair C during masturbation.

Users U1 and/or U2 can masturbate in a posture in which they lean back into the chair C and put their feet on a rest (not shown), and in this case, the user can masturbate in a more comfortable posture.

Figure 15:
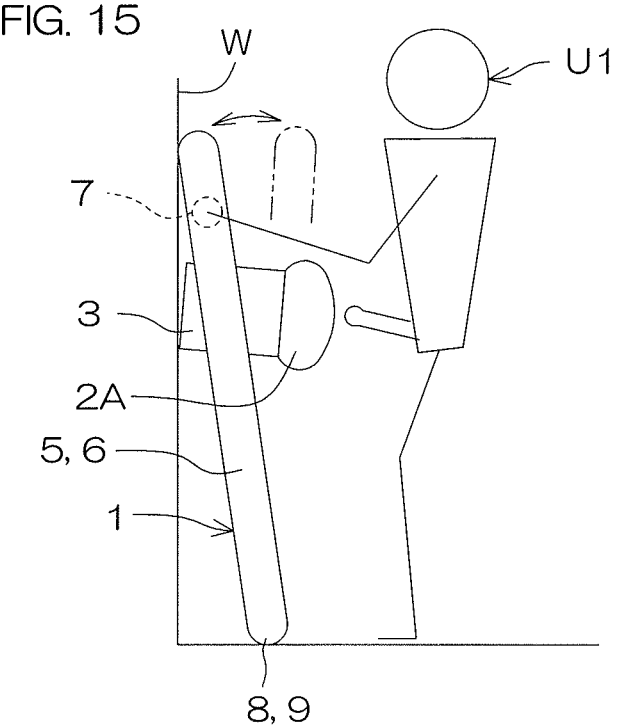
FIG. 15 is a schematic view showing another method for using the sex toy holder in the first usage pattern of this sex toy holder.

A user can use the sex toy holder 1 for masturbation not only in a posture in which the user sits on the chair C but also in a posture in which the user stands up. FIG. 15 is a schematic view showing another method for using the sex toy holder 1 in the first usage pattern of the sex toy holder 1. As shown in FIG. 15, the sex toy holder 1 is propped against a wall W or the like. The user U1 stands up to face the sex toy holder 1, and inserts his male genitalia into the inside of the sex toy 2A for a male. Then, in this state, the user U1 rocks his hips to reciprocate his male genitalia back and forth with respect to the sex toy 2A for a male. Accordingly, the user U1 can obtain pleasure. During masturbation, the user may grip the fastening member 7, or may grip other portions (for example, the columns 5 and 6) of the sex toy holder 1.

According to the present preferred embodiment, in both of the first usage pattern and the second usage pattern, during masturbation (action to obtain sexual pleasure), the sex toy holder 1 is stood so that the two leg portions 8 and 9 are arranged side by side in the right-left direction, and in this state, the user grips the fastening member 7 and rocks the sex toy holder 1 in a reciprocating manner by using the two leg portions 8 and 9 as fulcrums. According to the reciprocating rocking of the sex toy holder 1, the sex toy 2 held by the sex toy holding device 3 reciprocates in the back and forth direction with respect to the user. At this time, the weight of the sex toy 2 is borne by the two leg portions 8 and 9 that function as fulcrums. Therefore, the burden on the arm of the user can be reduced. Accordingly, masturbation using the sex toy 2 can be performed while reducing the feeling of fatigue.

Since the sex toy holder 1 is reciprocated with two leg portions 8 and 9 as fulcrums, the sex toy holder 1 does not wobble, and the sex toy 2 can be reciprocated in a stable state. Therefore, masturbation using the sex toy 2 can be stably performed. Accordingly, the sex toy 2 reciprocates in a stable locus. Thus, as a result of reciprocating motion of the sex toy 2 while reducing the feeling of fatigue and/or in a stable state, the user can concentrate on masturbation and obtain greater sexual pleasure.

Further, in an extending direction (right-left direction) of the fastening member 7 (gripping portion), the center C1 of the fastening member 7 and the center C2 between the two leg portions 8 and 9 match each other, so that in a usage state for masturbation, the load on the sex toy holder 1 in a state where a sex toy is attached thereto can be dividedly borne by the two leg portions 8 and 9. Accordingly, the reciprocating rocking of the sex toy holder 1 can be made more stable.

Also, in order to reciprocate the sex toy 2, the sex toy holder 1 is manually rocked in a reciprocating manner, so that as compared with the case where the sex toy 2 is reciprocated by using power of an electric actuator such as a motor, masturbation can be performed without producing great noise.

Since the fastening member 7 extends in the right-left direction, the user can easily grip the fastening member 7 with one hand, and can perform an operation to rock the sex toy holder 1 in a reciprocating manner with one hand.

Also, by fastening the other side end portions 5b and 6b of the pair of columns 5 and 6 to each other by the fastening member 7 in a state where the sex toy holding device 3 is sandwiched between the pair of columns 5 and 6, the sex toy holding device 3 is supported by the pair of columns 5 and 6. Accordingly, the sex toy holding device 3 can be easily attached to the pair of columns 5 and 6.

In the sex toy holder 1, the sex toy holding device 3 can be supported by the pair of columns at an arbitrary height position in an arbitrary posture (position in a turning direction). Accordingly, the height position and the posture of the sex toy holding device 3 can be set so that the sex toy 2 is set in a user's desired posture at a desired position.

When a user moves the fastening member 7 toward the other side end edges (upper sides in FIG. 1 and FIG. 2) of the columns 5 and 6 with one hand, the degree of sandwiching the sex toy holding device 3 by the pair of columns 5 and 6 can be reduced, and according to this, the user can adjust the height position and/or the posture of the sex toy holding device 3 so as to obtain an appropriate stimulus. Accordingly, the height position and/or the posture of the sex toy holding device 3 (that is, the sex toy 2) can be smoothly adjusted in a short time. Therefore, the position, etc., of the sex toy 2 can be finely adjusted during masturbation.

The sex toy holding device 3 can hold both of the sex toy 2A for a male and the sex toy 2B for a female. Therefore, male and female partners can share the sex toy holder 1, and it is not necessary to separately prepare a sex toy holder to hold the sex toy 2A for a male and a sex toy holder to hold the sex toy 2B for a female, and this is advantageous in terms of cost and storage space.

Figure 16:
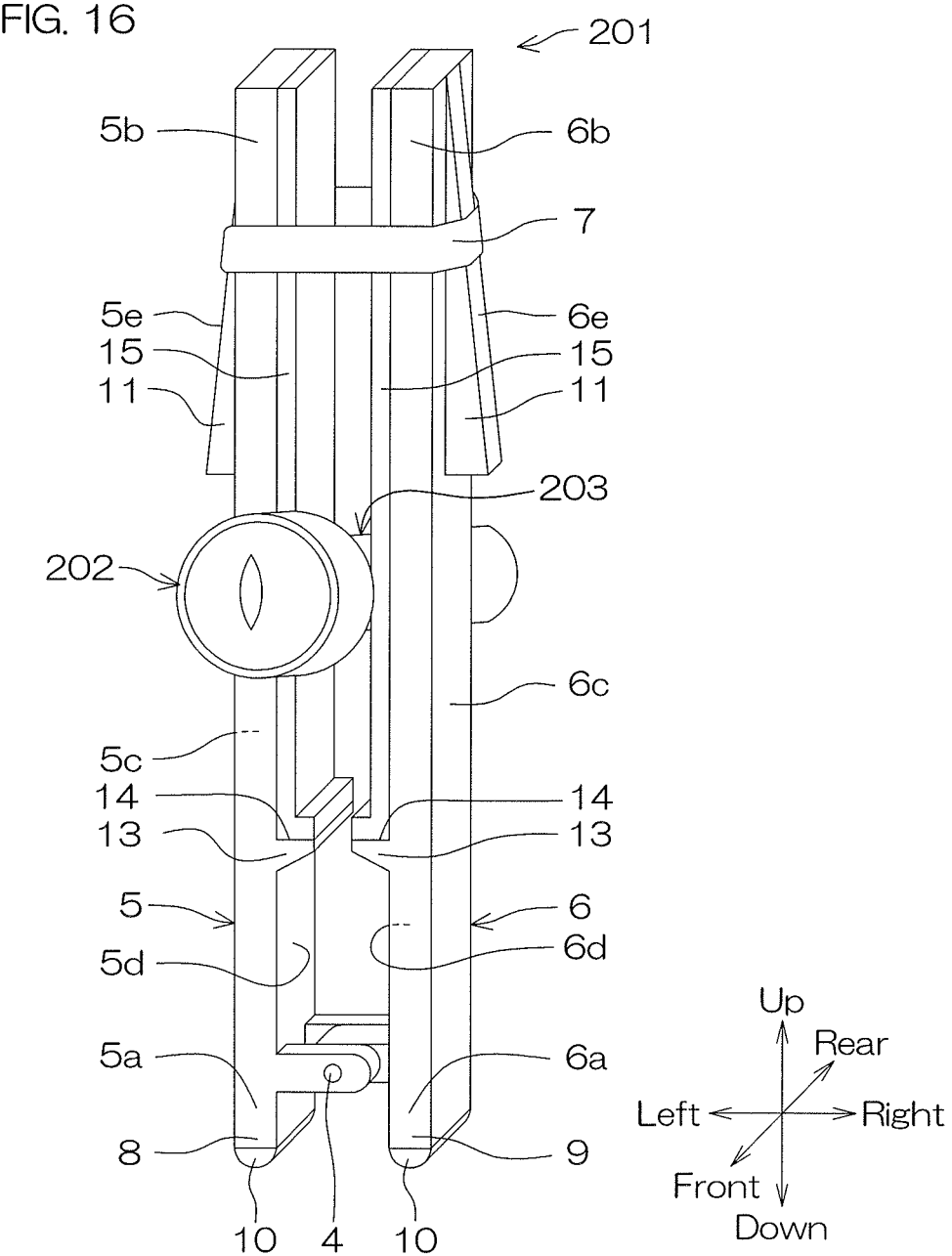
FIG. 16 is a perspective view of a sex toy holder according to a second preferred embodiment of the present invention.
Figure 17:
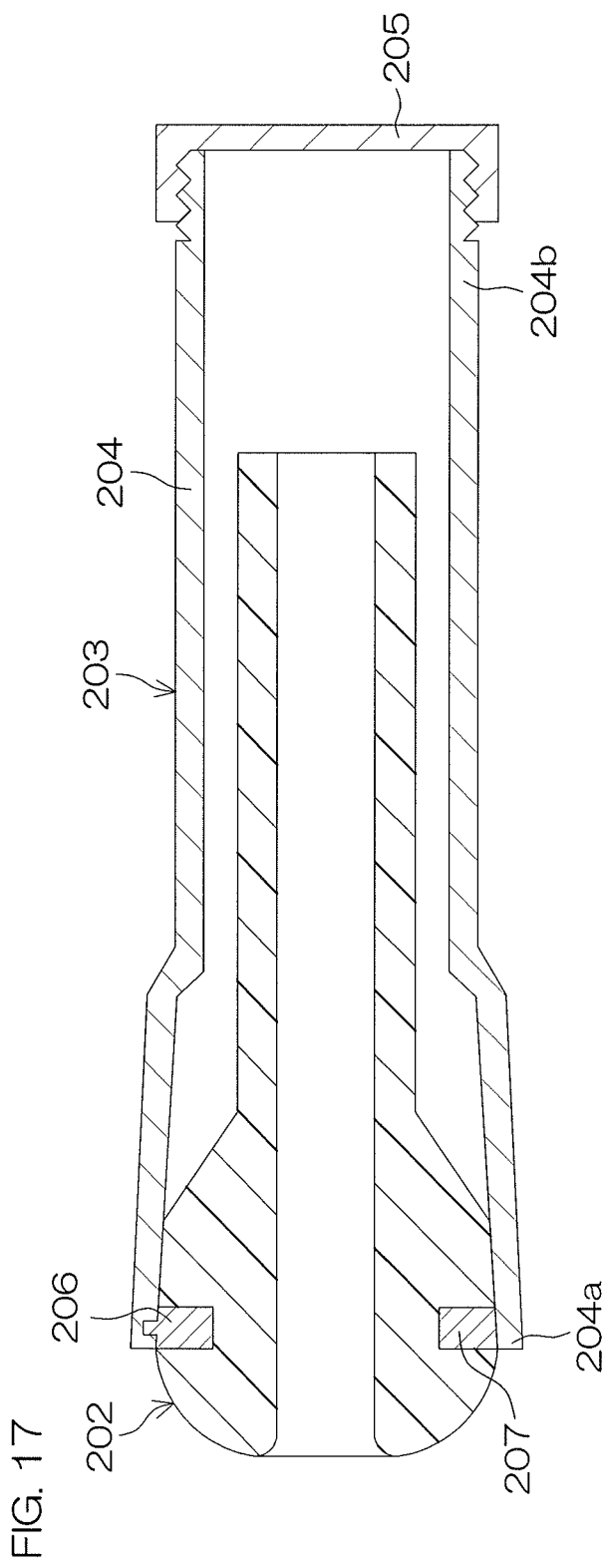
FIG. 17 is a sectional view showing an arrangement of a sex toy holding device to be fitted to the sex toy holder.

FIG. 16 is a perspective view of a sex toy holder 201 according to a second preferred embodiment of the present invention. FIG. 17 is a sectional view showing an arrangement of a sex toy holding device 203 to be fitted to the sex toy holder 201. The sex toy holding device 203 is a distribution item that is distributed as a product in a market.

The sex toy holder 201 shown in FIG. 16 and FIG. 17 is different from the sex toy holder 1 mainly in that the sex toy holder 201 does not include a sex toy holding device. The sex toy holder 201 is distributed in a market without a sex toy holding device. Also, the sex toy holding device 203 incorporating a sex toy 202 (for example, a sex toy for a male in FIG. 17) is retrofitted to the sex toy holder 201. The user masturbates using the sex toy holder 201 and the sex toy holding device 203.

The sex toy holding device 203 includes a cylindrical main body portion 204 opened to the front and rear sides, a lid 205 that closes a rear end portion 204b of the main body portion 204, and a fitting ring 207 fitted and fixed into a front end portion 204a of the main body portion 204. In a state where the sex toy 202 is accommodated in the main body portion 204, the fitting ring 207 is fitted in a groove 206 provided on the surface of the sex toy 202, and accordingly, the sex toy 202 is prevented from coming off from the main body portion 204. The sex toy holding device incorporating a sex toy is not limited to the sex toy holding device 203, but may be a sex toy holding device having a shape and structure different from that of the sex toy holding device 203. That is, a sex toy holding device which has a shape and structure that can be held (sandwiched) by the sex toy holder 201 and incorporates a sex toy can be used in place of the sex toy holding device 203.

Figure 18:
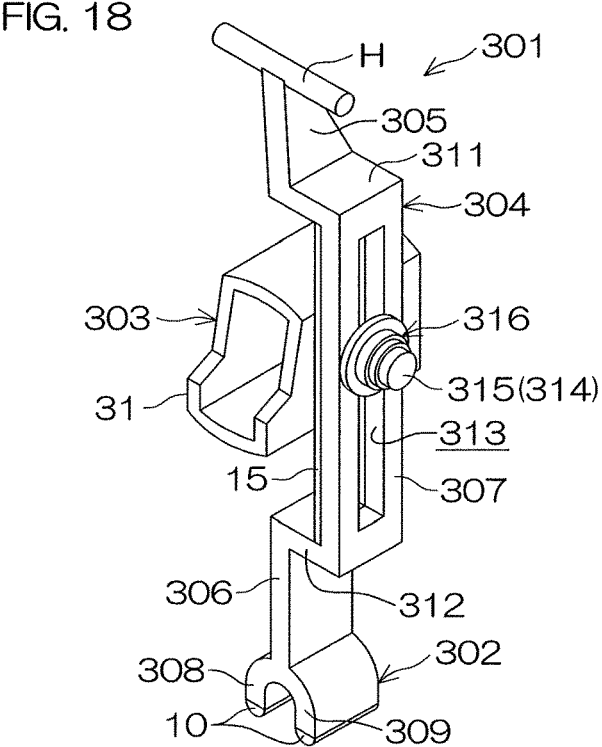
FIG. 18 is a perspective view of a sex toy holder according to a third preferred embodiment of the present invention.
Figure 19:
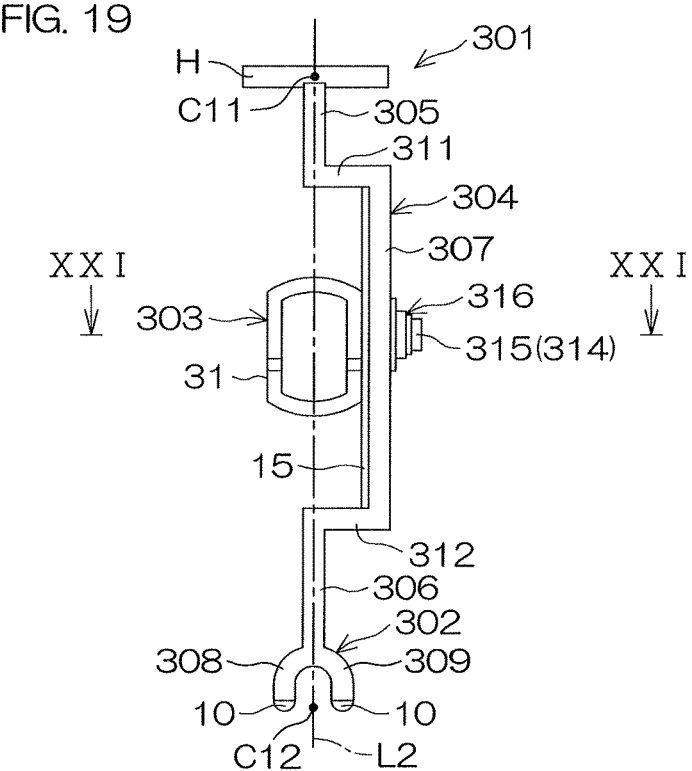
FIG. 19 is a front view of the sex toy holder.
Figure 20:
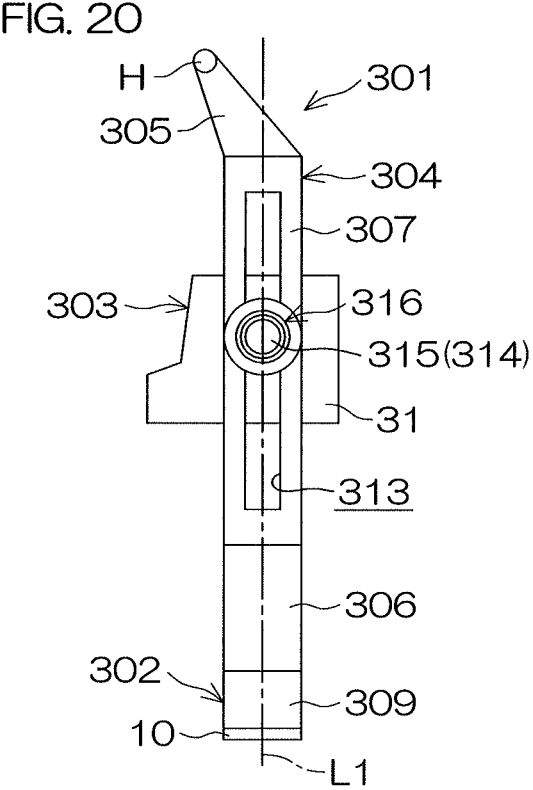
FIG. 20 is a right side view of the sex toy holder.
Figure 21:
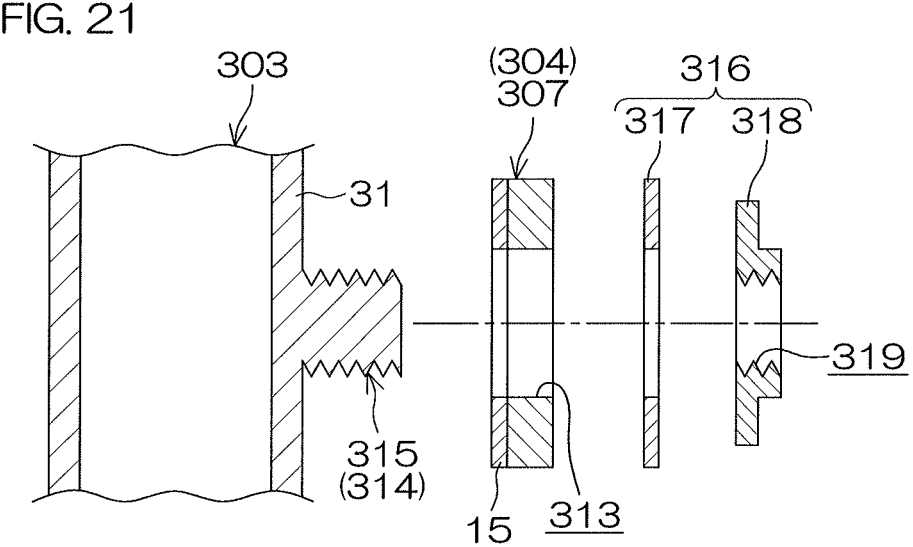
FIG. 21 is a sectional view for describing fastening of a holding device to a main body arm by a fastening unit.

FIG. 18 is a perspective view of a sex toy holder 301 according to a third preferred embodiment of the present invention. FIG. 19 is a front view of the sex toy holder 301. FIG. 20 is a right side view of the sex toy holder 301. FIG. 21 is a sectional view for describing fastening of the sex toy holding device 303 to a middle vertical column 307 by a fastening unit 316. FIG. 21 is a view of FIG. 19 from the cutting plane line XXI-XXI.

In FIG. 18 to FIG. 21, a portion common in the first preferred embodiment (preferred embodiment shown in FIG. 1 to FIG. 15) described above is designated by the same reference sign as in FIG. 1 to FIG. 15, and description thereof will be omitted.

The sex toy holder 301 includes a leg portion unit 302 including two leg portions 308 and 309, a handle (gripping portion) H that a user grips, and a support portion (joining portion) that supports (joins) the leg portions 308 and 309 and the handle H. The sex toy holder 301 is different from the sex toy holder 1 mainly in that the sex toy holder 301 includes one columnar support 304 in place of the pair of columns 5 and 6.

The columnar support 304 assumes a shape of a crank in a front view. The columnar support 304 includes integrally an upper vertical column 305 having an upper end to which the handle H is fixed, a middle vertical column 307 disposed between the upper vertical column 305 and a lower vertical column 306 in the up-down direction and extending in the vertical direction, the lower vertical column 306 having a lower end to which the leg portion unit 302 is fixed, an upper horizontal column 311 that joins a lower end of the upper vertical column 305 and an upper end of the middle vertical column 307, and a lower horizontal column 312 that joins an upper end of the lower vertical column 306 and a lower end of the middle vertical column 307.

The handle H assumes a shape of a rod extending in the right-left direction. As shown in FIG. 20, the handle H is disposed forward from a vertical axial line L1 passing through the central portion of the middle vertical column 307 in a right side view. A center C11 in the right-left direction of the handle H is fixed to the upper end of the upper vertical column 305.

The first leg portion 308 and the second leg portion 309 are leg portions to stand the sex toy holder 301. The first leg portion 308 and the second leg portion 309 are coupled integrally to each other to form the leg portion unit 302. The leg portion unit 302 is in an inverted U shape in a front view. The leg portion unit 302 is fixed to the lower end of the lower vertical column 306 so that a center C12 in the right-left direction between the first leg portion 308 and the second leg portion 309 matches the lower vertical column 306 in the right-left direction. The handle H, the columnar support 304 and the leg portion unit 302 are formed by using wood, a synthetic resin or metal, and have high rigidity.

As shown in FIG. 19, in the right-left direction (predetermined direction), the center C11 of the handle H (gripping portion) and the center C12 between the first and second leg portions 308 and 309 match each other. The upper vertical column 305 and the lower vertical column 306 match a line segment L2 connecting the center C11 and the center C12 in a front view, however, the middle vertical column 307 deviates laterally from the line segment L2 connecting the center C11 and the center C12 in a front view. The middle vertical column 307 has a slot 313 long in the vertical direction.

The sex toy holder 301 further includes a sex toy holding device 303 to hold the sex toy 2 (refer to FIG. 1). The sex toy holding device 303 includes the main body portion 31 according to the first preferred embodiment (refer to FIG. 5, additionally), and a support unit 314 to make the main body portion 31 be supported by the middle vertical column 307. The support unit 314 is a male screw portion 315 provided integrally with the main body portion 31 as shown in FIG. 21. The arrangement of the sex toy holding device 303 is in common with the sex toy holding device 3 according to the first preferred embodiment (refer to FIG. 1) except that the sex toy holding device 303 includes the support unit 314. In a front view, the centers of the openings of the main body portion 31 of the sex toy holding device 303 (the opening on the front side and the opening on the rear side) are included in a line segment connecting the line segment L2.

The sex toy holder 301 further includes a fastening unit 316 to fasten the sex toy holding device 303 to the middle vertical column 307. The fastening unit 316 includes, as shown in FIG. 21, a washer 317 that is fitted to the male screw portion 315 via the slot 313, and a nut 318 that is fitted to the male screw portion 315 via the slot 313 and the washer 317. The nut 318 has a female screw 319 that is screw-fitted to the male screw portion 315. In a state where the male screw portion 315 is inserted into the slot 313, the washer 317 and the nut 318 are fitted from the opposite side, and the nut 318 is tightened, and accordingly, the sex toy holding device 303 can be fixed to the support unit 314.

This third preferred embodiment brings the same operation and effect as those described in relation to the first preferred embodiment.

One of the features of this third preferred embodiment is that the main body portion 31 includes the upper vertical column 305 and the lower vertical column 306 that match the line segment L2 in a front view, and the middle vertical column 307 deviating laterally from the line segment L2 in a front view.

Another one of the features of this third preferred embodiment is that the handle H is disposed forward from the vertical axial line L1 in a right side view. Since the handle H is disposed in this manner, a user can easily rock the sex toy holder 301 in a reciprocating manner while gripping the handle H.

Three preferred embodiments of the present invention are described above, and the present invention can be carried out by still other embodiments.

For example, as shown in FIG. 22, a cylindrical member 300 having a cylindrical shape may be fitted on the sex toy 2A for a male. The cylindrical member 300 is formed by using, for example, the same material as that of the sex toy 2A for a male. As shown in FIG. 22, in a case where the sex toy 2A for a male is larger than the volume of the first accommodation chamber 34, the cylindrical member 300 may be used as a spacer to fill an extra space. Also, since the cylindrical member 300 fitted on the sex toy 2A for a male narrows the hollow portion 51 of the sex toy 2A for a male, the force of the sex toy 2A for a male to tighten a male genitalia can be improved, and as a result, the degree of user's (male user's) pleasure during masturbation can be improved.

In the first and second preferred embodiments, the sectional shapes of the tapered projections 11 in a plan view are not limited to those described above. That is, sectional shapes of the columns 5 and 6 in the other side end portions 5b and 6b are not limited to T shapes, and may be I shapes, or the side edges 5e and 6e may be formed to be arc-shaped in section.

Also, in the first and second preferred embodiments, both of the side edge 5e of the first column 5 and the side edge 6e of the second column 6 are provided with tapers 12, however, the taper 12 may be provided on only one of the side edges 5e and 6e.

Also, in the first and second preferred embodiments, the tapers 12 may be provided so that the side edges 5e and 6e on the sides not facing each other become narrower toward one side end portions 5a and 6a. Alternatively, the tapers 12 may not be provided.

Also, in the first and second preferred embodiments, the fastening member 7 may not fasten the other side end portions 5b and 6b but portions close to one sides relative to the other side end portions 5b and 6b.

Also, in the first and second preferred embodiments, the fastening member 7 may be provided to be unremovable from the pair of columns 5 and 6. In this case, the fastening member 7 may be formed of a metal fitting, etc.

Also, in the first and second preferred embodiments, the gripping portion that a user grips may be provided separately from the fastening member 7 in the sex toy holders 1 and 201.

The sex toy holders 1, 201, and 301 are described as unisex, however, they may be exclusively for males or females. In this case, both of the first and second accommodation chambers 34 and 35 of the sex toy holding device 3 may be used to accommodate the sex toy 2A for a male, or both of these may be used to accommodate the sex toy 2B for a female.

The sex toy holding devices 3 of the sex toy holders 1, 201, and 301 may not be arranged to be capable of accommodating a plurality of sex toys 2, but may be provided to be capable of accommodating only one sex toy 2.

Arrangements of the sex toy holders 1, 201, and 301 are not limited to those described above, and they are only required to include two leg portions 8 and 9 or 308 and 309, a gripping portion to be gripped by a user, and a support portion that supports (joins) the leg portions 8 and 9 or 308 and 309 and the gripping portion. Also, in the right-left direction (predetermined direction), the center C1 or C11 of the gripping portion and the center C2 or C12 between the first and second leg portions 8 and 9 or 308 and 309 are required to match each other.

The sex toy holders 1, 201, and 301 are used not only for masturbation, and may also be used by a plurality of users to bring sexual pleasure to one user among them.

Although the preferred embodiments of the present invention have been described in detail, they are merely specific examples used to clarify the technical contents of the present invention. Therefore, the present invention shall not be construed as being restricted to these specific examples and shall be limited only by the scope of attached claims of the present invention.

This application corresponds to Japanese Patent Application No. 2016-201861 filed on Oct. 13, 2016 in the Japan Patent Office, and entire disclosures of the application are herein incorporated by reference.

What is claimed is:

1. A sex toy holder that is provided to be capable of holding a sex toy, and is used for performing an action using the sex toy to obtain sexual pleasure, comprising:
    a gripping portion that is capable of being gripped by a user during the action, and linearly extends along a first direction;
    two leg portions, respectively having contact portions, arranged side by side at a distance along the first direction and being capable of contacting a floor by the contact portions during the action, the two leg portions being provided so that a center of the gripping portion and a center between the two leg portions are aligned with respect to the first direction; and a support portion that connects the two leg portions and the gripping portion and is capable of supporting the sex toy, wherein the gripping portion and the support portion are provided so as to reciprocate the sex toy in a second direction orthogonal to a plane including the first direction, using the contact portions as fulcrums, a distance between the gripping portion and each of the leg portions is longer than a distance between the two leg portions, and the action using the sex toy is performed by reciprocating the gripping portion and the support portion along the second direction while bringing the two leg portions into contact with the floor, using the contact portions as fulcrums.

2. The sex toy holder according to claim 1, further comprising:

a sex toy holding device to hold the sex toy, wherein the support portion supports the sex toy holding device.

3. The sex toy holder according to claim 2, wherein the support portion supports the sex toy holding device so that the sex toy holding device is movable up and down and/or changeable in posture.

4. The sex toy holder according to claim 1, wherein the support portion has one end portion and an other end portion, the two leg portions are disposed at the one end portion of the support portion, and the gripping portion is disposed at the other end portion of the support portion.

5. A sex toy holder that is provided to be capable of holding a sex toy, and is used for an action using the sex toy to obtain sexual pleasure 2, comprising:

a gripping portion that is capable of being gripped by a user during the action, and extends along a predetermined direction; the gripping portion including a fastening portion;

two leg portions, respectively having contact portions, arranged side by side at a distance along the predetermined direction and being capable of contacting a floor by the contact portions, the two leg portions being provided so that a center of the gripping portion and a center between the two leg portions are aligned with respect to the predetermined direction; and a support portion that connects the two leg portions and the gripping portion and is capable of supporting the sex toy, wherein the support portion includes a pair of columns, each of the columns having one of the leg portions disposed at one end thereof, an other end thereof being fastened to the one end by the fastening portion.

6. The sex toy holder according to claim 5, wherein the fastening portion includes a ring member that encloses the pair of columns, and each of the columns has a taper portion in which a width in a direction orthogonal to an extending direction of each the columns increases along the extending direction.

7. A sex toy holder that is provided to be capable of holding a sex toy, and is used for an action using the sex toy to obtain sexual pleasure, comprising:

a gripping portion that is capable of being gripped by a user during the action, and extends along a predetermined direction;

two leg portions, respectively having contact portions, arranged side by side at a distance along the predetermined direction and being capable of contacting a floor by the contact portions, the two leg portions being provided so that a center of the gripping portion and a center between the two leg portions are aligned with respect to the predetermined direction; and a support portion that connects the two leg portions and the gripping portion and is capable of supporting the sex toy; and a sex toy holding device to hold the sex toy, wherein the support portion supports the sex toy holding device, the support portion includes a pair of columns, each of the columns having one of the leg portions disposed at one end thereof, and being joined to each other at an other end thereof, and the sex toy holding device is supported by the columns by fastening the other end of said columns to each other in a state where the sex toy holding device is sandwiched between the pair of columns.

* * * * *